United States Patent [19]

Kimberling et al.

[11] 4,220,155
[45] Sep. 2, 1980

[54] APPARATUS FOR SPAYING LARGE ANIMALS

[75] Inventors: Cleon V. Kimberling; Gary P. Rupp, both of Fort Collins, Colo.

[73] Assignee: Colorado State University Research Foundation, Fort Collins, Colo.

[21] Appl. No.: 904,982

[22] Filed: May 11, 1978

[51] Int. Cl.² .................................. A61B 17/32
[52] U.S. Cl. ............................ 128/306; 128/305
[58] Field of Search .......... 128/754, 751, 749, 752, 128/753, 305, 306; 30/140

[56] References Cited

U.S. PATENT DOCUMENTS

| | | | |
|---|---|---|---|
| 1,585,934 | 5/1926 | Muir | 128/754 |
| 1,837,503 | 12/1931 | Thostenson | 128/305 |
| 1,867,624 | 7/1932 | Hoffman | 128/305 X |
| 3,762,416 | 10/1973 | Moss et al. | 128/305 |
| 3,844,272 | 10/1974 | Banko | 128/753 |
| 3,857,384 | 12/1974 | Watson | 128/749 |

Primary Examiner—Robert W. Michell
Assistant Examiner—Michael H. Thaler
Attorney, Agent, or Firm—Edwin L. Spangler, Jr.

[57] ABSTRACT

This invention relates to a surgical tool for use in removing the ovaries from large animals that is characterized by a pair of telescoped tubes, the inner tube of the pair terminating in a pointed end movable from a retracted position recessed inside the outer to an extended position projecting therebeyond. The inner tube is also rotatable within the outer tube so as to bring a pair of oval-shaped openings into registry with one another, so as to receive the ovaries to be removed one at a time. These openings have knife-edged margins effective to excise the ovary inside the tubes upon rotation of the inner tube within the outer. A plunger is also housed within the inner tube effective upon extension from a normally retracted position to push an excised ovary into a storage area behind the point of the inner tube thus clearing the opening therein to receive the second one. The invention also encompasses the novel method for removing the ovaries from large animals which comprises inserting the tool into the vagina, extending the pointed end of the inner tube and puncturing the vaginal wall therewith, retracting the point and inserting the tool into the abdomen with the openings therein in registry with one another, manipulating the first of the two ovaries per rectum into the openings and rotating the inner tube relative to the outer to excise same, and removing the tool.

4 Claims, 7 Drawing Figures

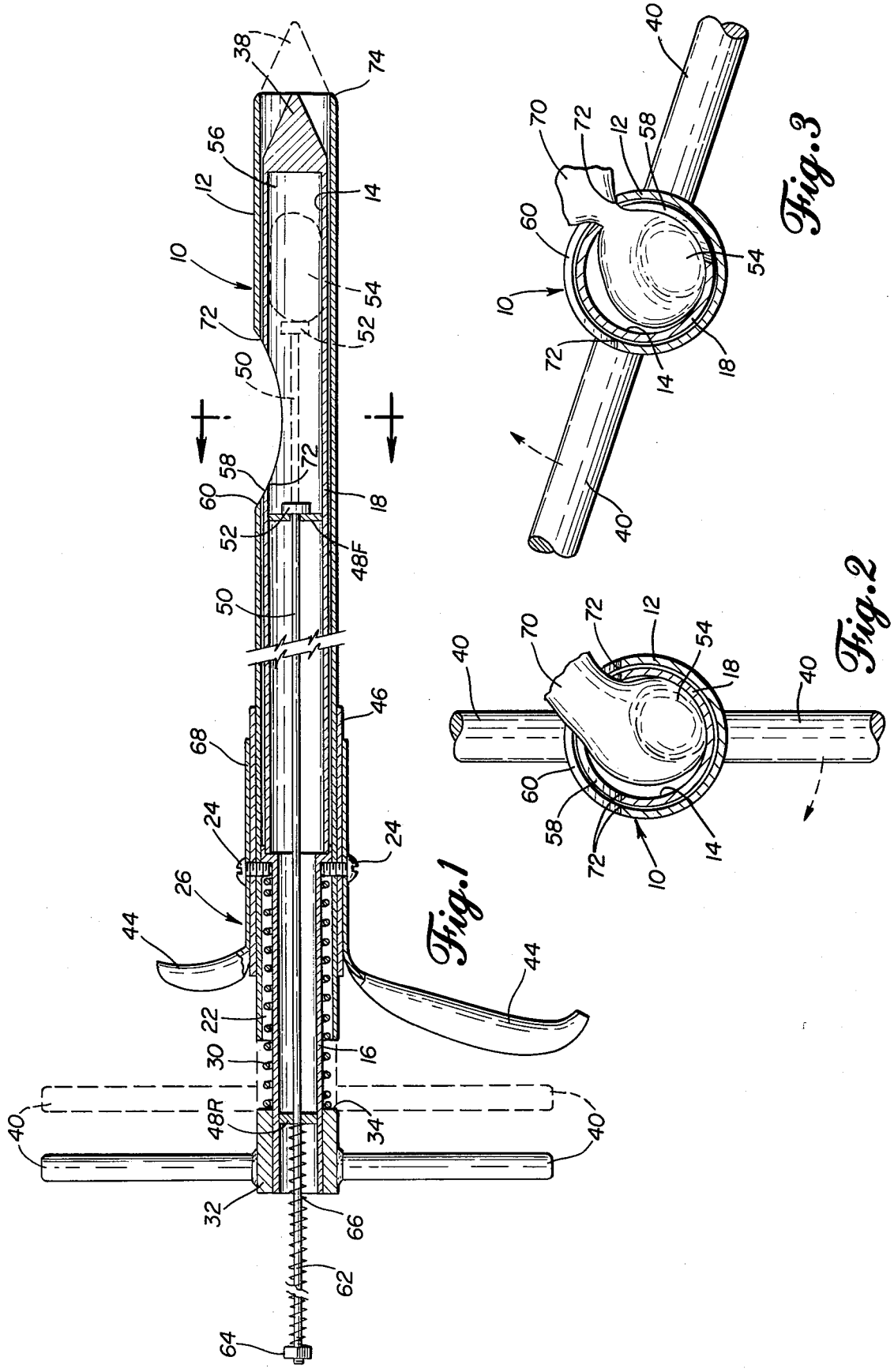

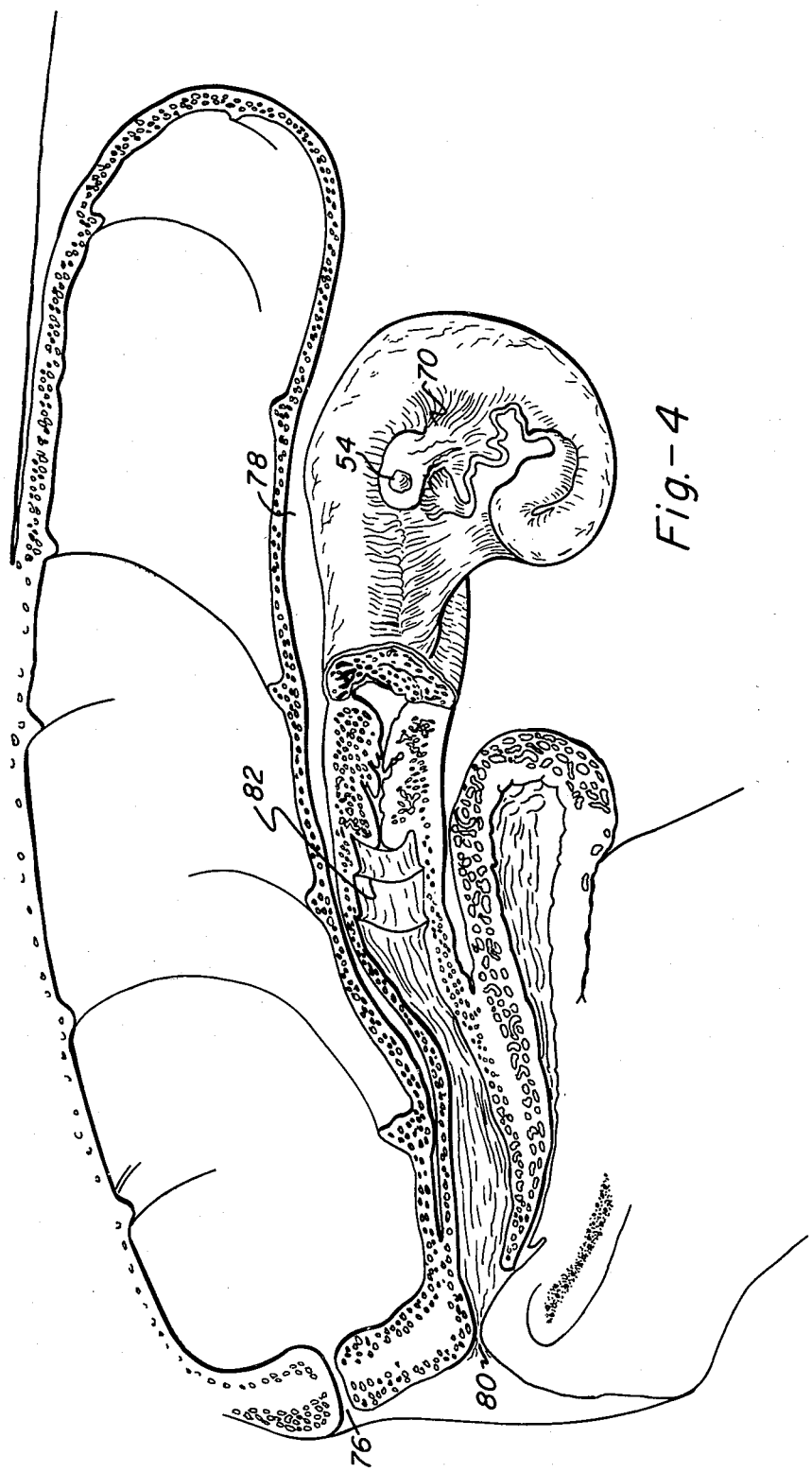

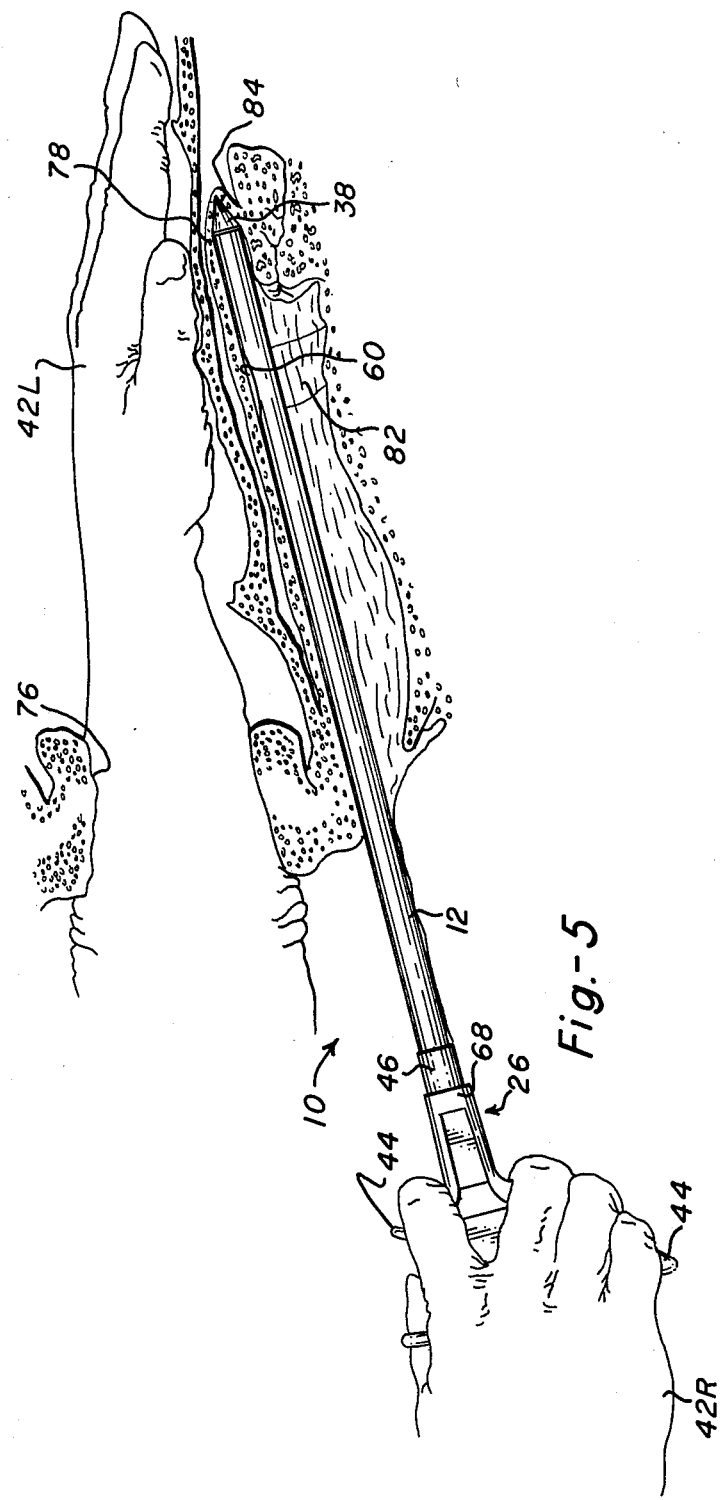

APPARATUS FOR SPAYING LARGE ANIMALS

The present invention has, as its sole purpose that of performing ovariectomies or the so-called "spaying" of large animals. Obviously, this procedure is performed upon the female of the species to prevent her from becoming pregnant.

The tool, as well as the method of using same, are confined to rather large animals like cattle and horses since manual manipulation per rectum is necessary and such techniques cannot be employed with the smaller species without risking serious injury to the animal. For practical purposes, the use of the technique will probably be largely confined to domestic animals although from an anatomical standpoint, both the technique and the tool will work on any large animal. Wild animals are, of course, somewhat difficult to restrain; however, if they could be tranquilized and handled in such a way as to not injure themselves or their handlers, the technique forming the subject matter hereof may have some application in game management where the range is limited and the natural predators are scarce or nonexistent. Zoo animals and those on wild animal farms are probably sufficiently domesticated to permit the techniques described herein to be used successfully; however, the emphasis in such animals is generally that of encouraging procreation of the species, not limiting it.

Ovariectomies have, of course, been performed for many years. Two basically different approaches have been used, one called "laparotomy" requiring direct entry into the abdomen while the other, "culpotmy" calls for abdominal entry through the dorsal vagina. While different, these prior art approaches are also similar in certain respects, namely, both require incisions large enough to receive the veterinarian's hand so that he or she can grab ahold of the ovary while excising it inside the abdomen.

Both of these methods are beset by many problems among which are complicated pre-surgical procedures. Proper restraint of the animal is of prime concern because the surgical procedure to be performed is lengthy, especially when compared with the technique of the instant invention. In addition, the site of the incision must be carefully prepared to reduce the danger of infection. Lastly, the complexity and time-consuming nature of the surgery demands that the animal be extensively anesthetized.

The actual surgical procedure is reasonably simple and straight-forward were it not for the pre-surgical and post-surgical complications, the latter probably being the more serious of the two. For instance, protecting the site of the incision from fly infestations and other possible sources of infection is no small problem. A less direct, but nonetheless very significant aftermath of such a procedure is the weight loss in the animal resulting from the trauma attendant to major surgery of any kind.

It has now been found that these and other serious consequences of the prior art ovariectomization techniques can, in large measure, be eliminated by the simple, yet unobvious expedient of gaining entry to the abdomen with a special tool through fornix of the vagina at a point dorsal to the cervix while using manipulation per rectum to locate the ovaries and place them one at a time into a chamber within the tool where they are excised and retained for subsequent removal. Such a technique requires only a very small puncture-type incision which decreases to a small diameter quite rapidly. It is also located deep inside the animal's body where it heals quickly and is well protected from the usual sources of infection. Moreover, the incision is made in an area that requires no pre-surgical preparation of any kind.

The procedure can, under certain circumstances, even be carried out under local anesthesia and the usual post-surgical trauma, weight loss and other side effects of major surgery are kept at a minimum. While the surgery should only be performed by qualified veterinarians skilled in the dealing with large animals and experienced in manipulation per rectum, it is still far simpler, safer and faster than the existing ovariectomization techniques. Care must be exercised to prevent hemorrhaging or pertitonitis following unintentional perforation of the intestines; however, such risks are always present and they are no more formidable with the instant technique than those presently being used. While the risk of pregnancy occasioned by incomplete removal of the ovaries is probably somewhat greater then with the pre-existing method where the ovary is actually removed by sight rather than by feel alone, such increased risks are minimal especially in the hands of a skilled practitioner.

Primary advantages are, of course, increased speed resulting from very little advanced preparation and minimal aftercare. Also, what little advanced preparation and aftercare that is required can, for the most part, be performed by unskilled persons leaving only the final preparations and the actual procedure itself that require the skills of a qualified graduate veterinarian.

The surgical tool itself is simple, easy to manipulate and designed specifically for use in accordance with the unique ovariectomization method forming the subject matter hereof. While not essential, it is certainly desirable to make only a single entry into the abdominal cavity and the preferred version of the tool makes provision for storing one of the excised ovaries while the other is being cut free so that the single entry technique can be practiced.

Accordingly, it is the principal object of the present invention to provide a new and improved method and apparatus for performing ovariectomies on large animals.

A second objective is the provision of a surgical tool for the practice of the aforementioned method which, in its preferred form, requires only a single entry into the abdominal cavity and it consisting of nothing more than a small, easily healed puncture-type incision located deep inside the vagina.

Another object is to provide a method for spaying large animals which is fast, safe and effective; yet, requires little pre-surgical preparation or post-surgical care, especially on the part of the person performing the procedure.

Still another object is to provide an ovariectomization method that is relatively free of post-surgical complications, especially those occasioned due to infection brought about by invasion of the incision by external agents.

Additional objects are to provide a simple, yet unobvious, technique for spaying heifers and the like that is both reliable and easily mastered while, at the same time, being ideally suited for use under field, as opposed to clinical, conditions.

Further objects are to provide a unique ovariectomy instrument which is simple yet versatile, easy to use, relatively inexpensive, no problem to clean and sterilize, compact, rugged, lightweight and even somewhat decorative.

Other objects will be in part apparent and in part pointed out specifically hereinafter in connection with the description of the drawings that follows, and in which:

FIG. 1 is a longitudinal half section, portions of which have been broken away to conserve space, showing the inner tube in retracted position along with the plunger and the openings in the two telescoped tubes aligned to receive an ovary;

FIG. 2 is a section to an enlarged scale taken along line 2—2 of FIG. 1 showing an ovary about to be excised located inside the tool but eliminating the fixed handle subassembly so as to more clearly reveal the position of the movable handle;

FIG. 3 is a section like that of FIG. 2 and to the same scale but differing slightly therefrom in that the inner tube of the telescoped pair is shown rotated inside the outer one to the point where it has begun to cut the ovary free from the adjacent tissue;

FIG. 4 is a pictorial representation of the pertinent portions of both the rectal and vaginal openings in relation to one another and to the abdominal cavity where the ovaries are located;

FIG. 5 is a pictorial view like FIG. 4 and to the same scale showing the tool inserted into the vagina with the inner tube extended to expose the pointed end thereof preparatory to puncturing the abdominal wall;

Figure 6:
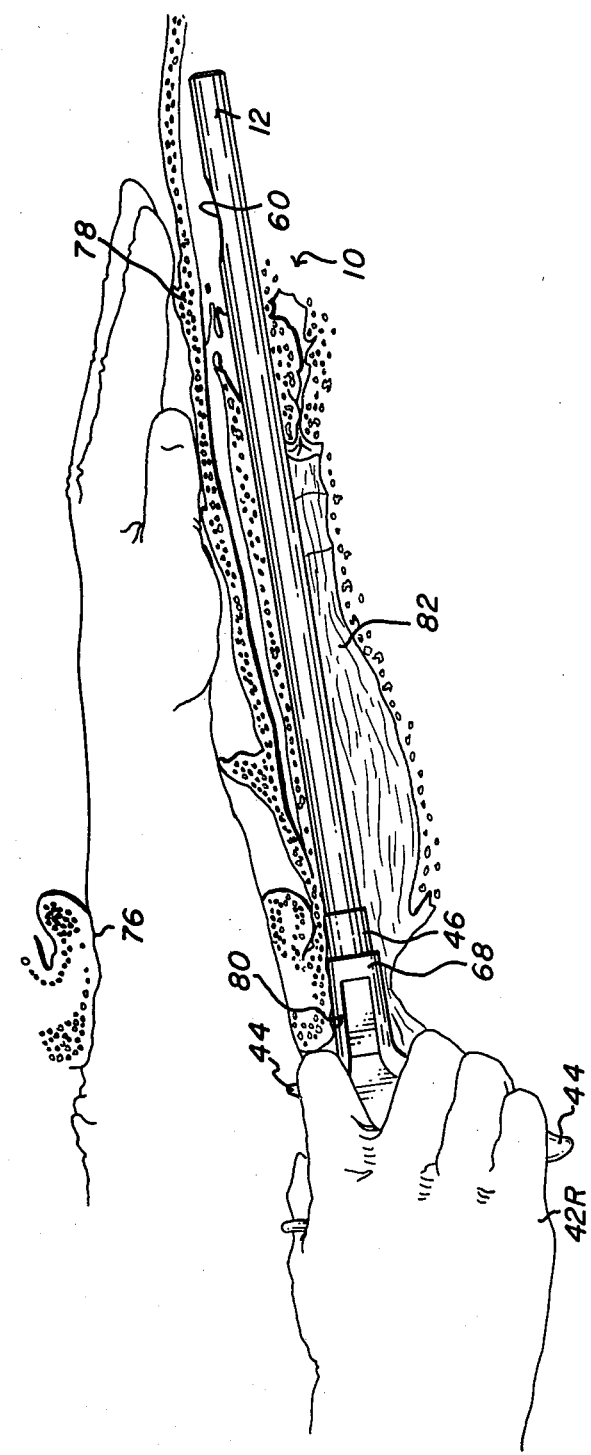
Figure 7:
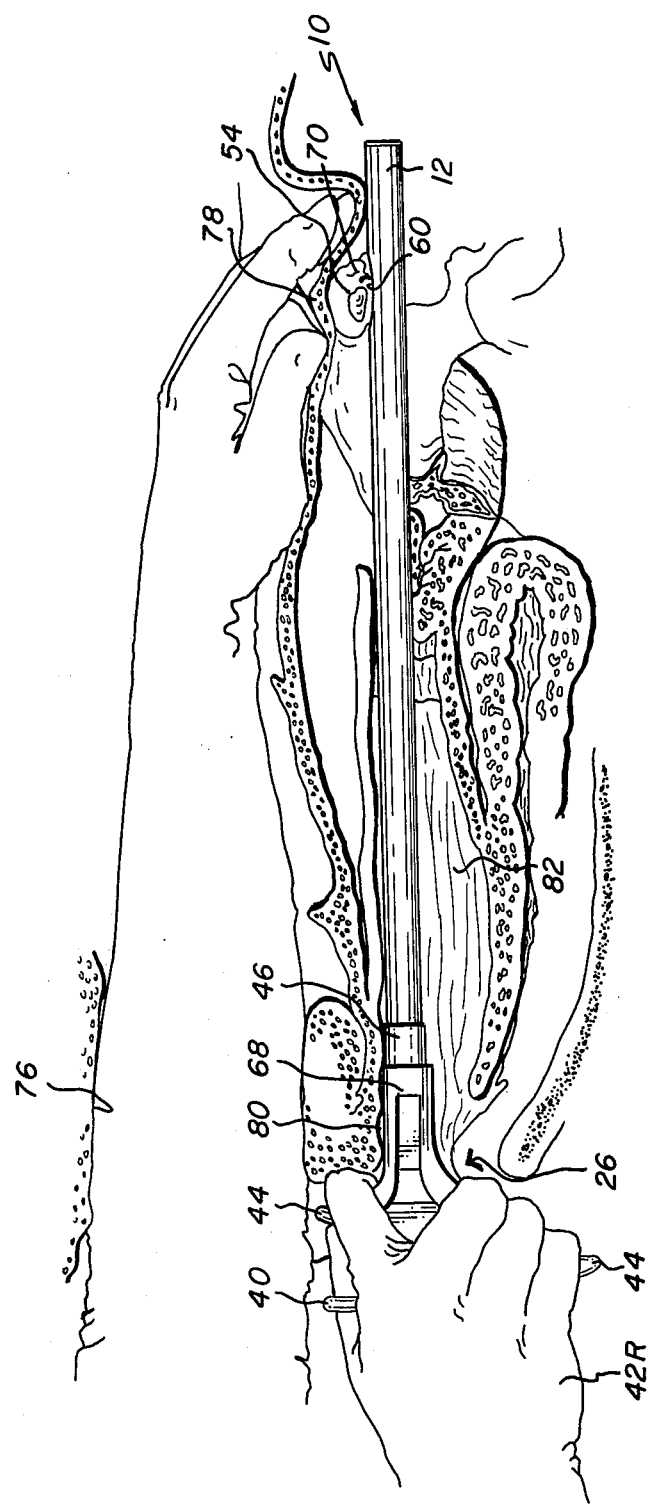

FIG. 6 is a pictorial view like FIGS. 4 and 5 and to the same scale showing the tool with its pointed end retracted but passed through the puncture opening it made into the abdominal cavity; and, FIG. 7 is still another pictorial view like the three preceding figures and to the same scale showing the next step in the ovariectomization procedure during which the ovaries are manipulated one at a time per rectum into the aligned openings in the telescoped tubes preparatory to cutting them free.

The surgical tool and its mode of operation can best be seen in FIGS. 1, 2 and 3 to which detailed reference will now be made, the aforesaid tool having been broadly designated by reference numeral 10. A pair of telescoped tubes 12 and 14 are arranged one inside the other for relative rotational movement as well as limited relative longitudinal movement. The outer of the two telescoped tubes 12 defines a fixed barrel within which the inner tube 14 moves. The inner tube is necked down to produce a section 16 of reduced diameter at its rear end separated from the main forward section 18 by rearwardly-facing annular shoulder 20. The inside surface of the outer tube lies in spaced relation to the reduced section 16 of the inner tube 14 thus cooperating with one another to produce an annular spring-receiving cavity 22 open at its rear end. A pair of fasteners 24 mount a fixed handle subassembly which has been broadly designated by numeral 26 on the barrel 12 adjacent its rear end. These fasteners project through the barrel wall and into cavity 22 where they define fixed forward abutments for loose-wound compression spring 30. A collar 32 is detachably connected to the rear end of the inner tube to provide a forwardly-facing shoulder 34 abutting the rear end of spring 30. Forward movement of the inner tube 14 relative to the outer tube or barrel 121 compresses spring 30 which normally biases the inner tube into the retracted position indicated by full lines in FIG. 1. In the fully retracted position shown, annular shoulder 20 separating the sections of the inner tube strikes fasteners 24 which thus constitute stops limiting the rearward excursion or travel of the inner tube.

The forward end 38 of the inner tube is shaped to produce a sharp pointed instrument capable of puncturing the abdominal wall, such instruments being known as "trocars." The trocar defined by the pointed inner tube 14 is normally retracted such that point 38 lies recessed inside the barrel. In the extended operative position shown by the phantom lines in FIG. 1 and full lines in FIG. 5, point 38 is exposed and projects beyond the forward end of the barrel.

Extension of the trocar-forming inner tube is accomplished by placing radially-extending rods 40 depending from collar 32 in the palm of the operator's hand 42R in the manner shown in FIG. 5 while grasping the fingerholds 44 projecting from sleeve 46 of the fixed handle subassembly 26. As the operator's hand closes, the inner tube will move into the extended phantom line position of FIG. 1 and the full line position of FIG. 5.

Inside the inner tube 14 arranged in axially-spaced relation are a pair of centrally-apertured guide plates 48 that receive pushrod 50 for relative reciprocating movement. The forward end of the pushrod is provided with a head 52 cooperating therewith to define a plunger effective upon actuation to move an excised ovary 54 forward into a storage pocket 56 lying between ovary-receiving openings 58 and 60 and pointed end 38. The retracted inoperative position of the plunger subassembly has been shown in full lines in FIG. 1 while the extended operative position thereof along with the severed ovary is shown in phantom lines. In the particular form shown, the rear end 62 of the pushrod is threaded to detachably receive fastener 64 that provides a movable abutment engaging the rear end of compression spring 66. The front end of the latter spring engages the rear face of the rear apertured guideplate 48R. Spring 66 normally biases the pushrod into its retracted position in precisely the same way that spring 30 acts to retract the trocar-forming inner tube 14. Head 52 engages the forward face of front guideplate 48F thus limiting the rearward excursion of the plunger subassembly.

The details of fixed handle subassembly 26 are fairly conventional and, for this reason, no useful purpose will be served by describing it in detail. It is sufficient to note that the fingerholds 44 both depend from a collar 68 (FIGS. 6, 7 and 8) encircling sleeve 46 and which slides onto the barrel 14. Fasteners 24 pass through the fingerholds, sleeve and barrel thus holding the fixed handle subassembly 26 in assembled relation.

FIGS. 1, 2 and 3 reveal the alignable oval-shaped openings 58 in the inner tube 14 and a like opening 60 in the outer one. As shown in FIGS. 1 and 2, with the inner tube 14 fully retracted inside the outer one, these openings become alignable with respect to one another upon rotation of the inner tube to the proper position. As shown, handles 40 lie in a plane bisecting opening 58 in the inner tube thus making it simple for the operator to orient the latter even when hidden inside the body. These openings are of a size that will receive most of the large animal ovaries to be excised, say approximately 1½ inches long by a half inch across. In the rare event that an oversize ovary is encountered which will not fit into the openings, it can be excised a piece at a time.

Looking particularly at FIGS. 2 and 3, it can be seen that once the ovary 54 is located inside the instrument, the inner tube 14 thereof need only be rotated relative to the outer tube 12 to sever it from the adjacent tissue 70. Knife-edged surfaces 72 border each opening with the trailing edge of the inner one coacting with the leading edge of the other in the manner shown in FIG. 3 to accomplish the desired cut. Manipulation of the fixed handles 40 with the thumb in a manner to rotate them while the fingers hold the fixed handle subassembly 26 stationary easily severs the ovary inside the instrument from the surrounding tissue. Once severed and the movable handles rotated 180°, the inner tube becomes effective to close the opening 60 in the outer tube thus trapping the severed ovary inside thereof; whereupon, pressing plunger 50 with the palm of the hand will push the ovary thus severed down into storage pocket 56 in the forward end of the inner tube. At this point, the handles 40 can be returned to their original position realigning openings 58 and 60 without danger of losing the ovary already excised.

Now, while the preferred mode of actuation to sever the ovary is that of rotating the inner tube relative to the barrel or outer one as has just been described, it is also mechanically possible to do so by moving the inner tube forward axially relative to the outer until the trailing edge of opening 58 passes by the leading edge of opening 60. In some respects, it is easier for the operator to move the inner tube forwardly overcoming the bias exerted by spring 30 than it is to rotate it while holding the outer tube stationary. There is, however, a serious drawback to this technique which mitigates against its use and that is the fact that pointed end 38 is projected forwardly out of the barrel into a position where it can damage internal organs within the abdominal cavity. Especially vulnerable are the intestines and the slightest puncture brings about peritonitis which is often fatal. With the trocar retracted, only the smoothly rounded edges 74 bordering the blunt end of the outer tube are in a position to cause injury and the chances are minimal. Accordingly, the preferred method of severing the ovary remains that of rotating the inner tube relative to the outer one.

Before explaining the details of the method it would, perhaps, be worthwhile to briefly outline the advance preparations that should be made as well as some of the precautions to be taken. To begin with, the animal must be large enough to permit rectal examination. In the case of heifers, one weighting around 500 pounds is usually large enough and, occasionally the technique can be used on smaller ones.

The animals upon which the ovariectomy are to be performed should be in good physical condition and free of disease, recent stress or any other probelm that might slow down its clotting time. No food or water should be given the animal for at least 24 hours prior to the time the procedure is to be performed. Also, the animal should be examined for pregnancy although this can be done at the time the genital examination is conducted just prior to initiating the ovariectomy.

The animal should be standing while the procedure is being performed, therefore, restraint of some kind is necessary such as, for example, in a cattle-working chute. Care should be exercised to not exert undue pressure on the abdomen because such pressure tends to force the intestines up into the pelvic area thus interfering with the spaying procedure.

Just prior to performing the spaying operation and with the animal suitably restrained, it is anesthetized locally and a rectal examination made to remove any remaining fecal material. The genital organs are also examined and the cervix and ovaries are located. Upon completion of such examinations and while the operator's arm is still in the rectum, the perineal and external genital area can be cleaned and disinfected.

Referring next to FIGS. 4-7, inclusive, the actual method of using the tool 10 to perform the ovariectomy will be set forth in detail. FIG. 4 is, of course, nothing more than an anatomical diagram revealing the placement of the organs and the relative positions of the pertinent body cavities in a large female animal, the particular one shown being that of a heifer.

The initial steps in the procedure are those revealed in FIG. 5 to which reference will now be made. One hand, the left (42L) as shown, is covered with a surgical glove and inserted through the anus 76 to a position alongside the wall of the abdomen 78 where the fingers can locate and minipulate the ovaries 54 into the aligned openings 58 and 60 in the tool once it is in place. With the left hand in this position, the previously noted genital examination cleansing and disinfecting operations are carried out. Then, with the left hand still in place, the other hand (42R) is used to insert the tool while the pointed end 38 remains retracted into the entrance 80 to the vagina 82. Using the left hand in the rectum, positioned just dorsal to the cervix, the forward end of the tool is guided into position against the vaginal fornix 84. Next, the movable handle 40 is actuated into the phantom line position of FIG. 1 to extend pointed end 38 thus transforming inner tube 14 into a trocar. At this point, it is advisable to use the left hand to move the rectum away from the vagina to prevent injury to the rectum. It is this position of the hands and tool that has been shown in FIG. 5.

A short sharp forward thrust of the tool with it held firmly against the vaginal fornix will bring about penetration through the vaginal wall into the abdominal cavity. Successful penetration is usually indicated by unrestricted movement of the tool. Immediately upon penetration of the abdominal cavity (FIG. 6) the trocar is released to its normally-retracted position.

With the instrument thus safely within the abdominal cavity, the left hand is employed as indicated in FIG. 7 per rectum to isolate one of the ovaries 54 and manipulate it into the openings 58 and 60 which resume their registered relation once the point 38 is retracted into the barrel defined by the outer tube 12. Once the ovary is inside the tool and the operator is sure that it is the only thing inside, i.e. the cutting edges 72 are clear of other tissue, then handles 40 are rotated while holding fixed handle subassembly 26 essentially stationary. Upon completion of between a quarter and a half turn, the ovary within the tool should be cut free of its connecting tissue 70. With the excised ovary thus encased inside the tool, the plunger subassembly that includes pushrod 50 can be actuated to move it forward into storage cavity 56 as shown by broken lines in FIG. 1.

Finally, the handles 40 are realigned with fingerholds 44 to reopen the ovary-receiving cavity and the whole process repeated with the remaining ovary except that it need not necessarily be pushed into the sotrage area before the tool is withdrawn. As the tool is removed, it leaves a small puncture incision which closes up and heals very quickly. Most significant, however, is its internal location where flies and other contaminants cannot reach it.

The procedure just described is fast, safe the relatively free of the usual complications associated with the spaying of large animals.

What is claimed is:

1. The surgical tool for excising the ovaries from large animals which comprises: an outer tubular member having an ovary-receiving opening in the wall thereof bordered by a sharpened inside edge, an inner tubular element telescoped within the outer tubular element cooperating therewith to define a close sliding fit for both relative axial and rotational movement, said inner tubular element terminating at one end in a point effective to puncture the wall of the animal's abdominal cavity, said inner tubular element having an ovary-receiving opening in the wall thereof bordered by a sharpened edge positioned and adapted to cooperate in aligned position with the sharpened edge of the opening in the outer tubular element upon relative movement therebetween to cut an ovary housed within the inner tubular element free of its connecting tissue, and said ovary-receiving opening of the inner tubular element being spaced from said point thereof a distance effective to leave a storage compartment therebetween of a size to house an excised ovary, first handle-forming means depending from the end of the inner tubular element opposite said pointed end thereof, said first handle-forming means being accessible beyond the adjacent end of the outer tubular element and adapted for use in reciprocating said inner tubular element between an extended position with its pointed end exposed beyond the corresponding end of said ouer tubular element and a retracted position withdrawn inside the latter, and said first handle-forming means also providing means for rotating the inner tubular element within said outer tubular element while the latter is held stationary, and a pushrod mounted for relative reciprocating movement within the inner tubular element between a retracted position on the opposite side of the ovary-receiving opening therein from the pointed end thereof and an extended position on the same side thereof, said pushrod being accessible from said opposite end of the inner tubular element and effective upon actuation with an excised ovary inside the latter to push same into said storage compartment.

2. The surgical tool as set forth in claim 1 in which: second handle-forming means are mounted on the end of the outer tubular element adjacent the first handle-forming means, said second handle-forming means being adapted to be grasped by the fingers of the operator's hand in a manner to hold said outer tube stationary while the thumb and palm of the same hand are manipulated to extend or rotate said inner tubular element.

3. The surgical tool as set forth in claim 1 wherein: spring means extending between spaced abutments on the inner tubular element and pushrod normally bias the latter into retracted position.

4. The surgical tool as set forth in claim 1 wherein: front and rear centrally-apertured guides are mounted in axially-spaced relation within the inner tubular element, the pushrod is mounted for axially-slidable movement within said apertured guides, and in which a head is provided on the pushrod position and adapted to engage the front guide and cooperate therewith to limit the retractable movement of said rod.

* * * * *